United States Patent [19]

Young, Jr. et al.

[11] Patent Number: 4,575,494
[45] Date of Patent: Mar. 11, 1986

[54] ALUMINA COMPOSITIONS USEFUL AS CATALYST SUPPORTS FOR ETHYLENE OXIDATION

[75] Inventors: Harold W. Young, Jr.; Oliver C. Ainsworth, Jr., both of Baton Rouge, La.; William E. Fry; Lawrence E. Neil, both of Angleton, Tex.

[73] Assignee: The Dow Chemical Company, Midland, Mich.

[21] Appl. No.: 578,256

[22] Filed: Feb. 8, 1984

[51] Int. Cl.[1] ............................................. B01J 20/04
[52] U.S. Cl. .................................... 502/243; 502/344; 502/348
[58] Field of Search ......................... 502/243, 348, 344

[56] References Cited

U.S. PATENT DOCUMENTS

| | | | |
|---|---|---|---|
| 2,499,675 | 3/1950 | Owen | 252/465 |
| 2,950,169 | 8/1960 | Murray et al. | 23/143 |
| 2,984,630 | 5/1961 | Braithwaite | 252/464 |
| 3,172,866 | 3/1965 | Belon | 252/463 |
| 3,222,129 | 12/1965 | Osment et al. | 23/141 |
| 3,223,483 | 12/1965 | Osment | 23/143 |
| 3,226,191 | 12/1965 | Osment et al. | 23/141 |
| 3,628,914 | 12/1971 | Grauffer | 23/143 |
| 3,664,970 | 5/1972 | De Malo | 252/454 |
| 3,804,781 | 4/1974 | Colgan | 252/463 |
| 3,856,708 | 12/1974 | Carithers | 252/463 |
| 3,907,512 | 9/1975 | Ziegenhain et al. | 23/293 A |
| 3,907,982 | 9/1975 | Leach | 423/630 |
| 3,928,236 | 12/1975 | Rigge et al. | 252/463 |
| 3,987,155 | 10/1976 | Ziegenhain | 423/628 |
| 3,997,476 | 12/1976 | Cull | 252/463 |
| 4,001,144 | 1/1977 | Pearson et al. | 252/463 |
| 4,010,115 | 3/1977 | Nielsen et al. | 252/454 |
| 4,012,425 | 3/1977 | Nielsen et al. | 260/348.5 R |
| 4,022,715 | 5/1977 | Bornfriend | 252/463 |
| 4,039,481 | 8/1977 | Kimura et al. | 252/464 |
| 4,039,561 | 8/1977 | Mitsuhata et al. | 260/348.34 |
| 4,066,575 | 1/1978 | Winnick | 252/475 |
| 4,098,874 | 7/1978 | Mitsche et al. | 423/628 |
| 4,123,385 | 10/1978 | Rebadat et al. | 252/414 |
| 4,139,494 | 2/1979 | Itoh et al. | 502/243 |
| 4,207,210 | 6/1980 | Kilty | 502/348 |
| 4,242,233 | 12/1980 | Ball et al. | 252/431 N |
| 4,248,741 | 2/1981 | Wernli et al. | 252/463 |
| 4,305,844 | 12/1981 | Vangerman et al. | 502/243 |
| 4,309,313 | 1/1982 | Barrett et al. | 252/455 Z |
| 4,350,616 | 9/1982 | Boussert | 252/463 |
| 4,375,571 | 3/1983 | Hart et al. | 502/344 |

FOREIGN PATENT DOCUMENTS

| | | | |
|---|---|---|---|
| 867185 | 11/1978 | Belgium | 502/348 |
| 2448449 | 4/1975 | Fed. Rep. of Germany | 502/348 |

*Primary Examiner*—Andrew H. Metz
*Assistant Examiner*—Helane Myers
*Attorney, Agent, or Firm*—A. C. Ancona

[57] ABSTRACT

An alumina support which contains cesium is prepared by adding a fusible compound of cesium to alumina along with known binders and porosity control agents. The cesium compound should be fusible below the temperature at which the alumina fuses. Such a support is especially useful as a support for a silver catalyst employed in the oxidation of ethylene to ethylene oxide.

13 Claims, No Drawings

ALUMINA COMPOSITIONS USEFUL AS CATALYST SUPPORTS FOR ETHYLENE OXIDATION

BACKGROUND OF THE INVENTION

Aluminas and alumina-silicates are well known to be useful as catalysts, adsorbents and catalyst supports. These materials are made by fusing high purity (99+%) aluminum oxide with or without silica (usually as sodium silicate). They may be very porous or non-porous and have a high or low surface area depending upon the use to be made of them. When used to support a catalyst the support may contain any porous, inert material which does not detrimentally influence the catalytic reaction wherein it is employed. An early patent describing a method of making a pelleted alumina catalyst is U.S. Pat. No. 2,499,675.

Representative of the method of making alumina supports is the following description found in U.S. Pat. No. 3,664,970. The particular support therein is said to be useful as a support for a silver catalyst employed in the oxidation of ethylene to ethylene oxide. For this purpose the support material comprises 90 percent or more by weight alpha alumina and 1 to 6 percent by weight silica. This composition is a preferred support material when combined with 0.1 to 0.4 percent by weight baryta.

In the process of making a support, the high-purity aluminum oxide, preferably in the alpha alumina phase, is throughly mixed with temporary and permanent binders. The temporary binders are thermally decomposable organic compounds of moderate to high molecular weight (i.e., molecular weights above about 250) which, on decomposition, produce the pore structure of the support. The permanent binders are inorganic clay-type materials having fusion temperatures below that of the alumina and are responsible for imparting mechanical strength to the finished support. Silica and baryta can also be added in quantity sufficient to obtain a finished support of the desired strength and composition. After thorough dry-mixing, sufficient water is added to the mass to form the mass into a paste-like substance. The catalyst support particles are then formed from the paste by conventional means such as, for example, high pressure extrusion, granulation or other ceramic forming processes. The particles are then dried and are subsequently fired at an elevated temperature which is in the range of 1,200° to 1,600° C.

In the firing step, the temporary binders are thermally decomposed to carbon dioxide and water and are volatilized, leaving voids in the support mass. These voids are the genesis of the pore structure of the finished support. Suitable temporary binders include such materials as the celluloses and substituted celluloses, e.g. cellulose itself, methylcellulose, ethylcellulose, and carboxyethylcellulose, stearates such as organic stearate esters, e.g. methyl or ethyl stearate, waxes and the like. As firing is continued, the temperature reaches the point at which the permanent binder (inorganic clay such as the kaolins or the ball clays) fuses. The catalyst support is then permitted to cool and, during cooling, the permanent binder sets, acting as a cement to bond the catalyst support particles, and thereby impart mechanical strength to the support and ensure maintenance of the pore structure.

Catalyst supports of desired characteristics can be readily produced by the foregoing procedure. Control of pore size, pore size distribution and porosity are readily affected by appropriate adjustment in known manner of the size of the starting alumina particles, and of the particle size and concentration of the temporary and of the permanent binders in the starting mixture. The larger the starting alumina particle size, the greater will be the porosity of the finished catalyst. The more homogenous in size are the alumina particles, the more uniform will be the pore structure. Similarly, increasing the concentration of the temporary binder will also increase the overall porosity of the finished catalyst support.

Earlier patents which describe the making of alumina supports are U.S. Pat. Nos. 2,499,675; 2,950,169 and 3,172,866. Other patents such as U.S. Pat. Nos. 3,222,129; 3,223,483 and 3,226,191 show the preparation of active aluminas. A particular alumina pellet having high mechanical strength is described in U.S. Pat. No. 3,628,914. Methods of making highly porous aluminas are disclosed in U.S. Pat. Nos. 3,804,781; 3,856,708; 3,907,512 and 3,907,982. Alumina carriers having high thermal stability are disclosed in U.S. Pat. No. 3,928,236. Other more recent improve ments in making catalyst carriers are found in U.S. Pat. Nos. 3,987,155; 3,997,476; 4,001,144; 4,022,715; 4,039,481; 4,098,874 and 4,242,233.

High purity alumina is preferred in order to avoid any extraneous elements, e.g. sodium, which might deleteriously affect the catalytic coating. This is especially true for those supports used to make silver catalysts for use in making ethylene oxide. Such high purity supports have been made, but most do not have as good crush strength as do the lower purity supports. Those high strength, high purity supports which have been made have low porosity which is undesirable in supports for use in EO manufacture. Supports used for silver catalysts employed in the oxidation of ethylene to ethylene oxide also are desirably of low surface area, i.e. less than about 1 $m^2/g$. It would, therefore, be highly desirable to have high purity, high porosity, low surface area supports of increased strength for use in making silver catalysts for EO manufacture.

A recent patent (U.S. Pat. No. 4,309,313) for a synthetic zeolite is for a composition containing silicon, aluminum, sodium and cesium or thallium oxides. It has utility as a sorbent and in separation and catalytic applications. This composition does not require the high temperatures that are employed in making the compositions of the present invention.

The use of cesium, among other alkali metals of Group I of the Periodic Table of the Elements, as a promoter for silver catalysts employed in the production of ethylene oxide by the partial oxidation of ethylene in the vapor phase is well known. Among relatively recent patents which claim such catalysts are U.S. Pat. Nos. 4,010,155; 4,012,425; 4,123,385; 4,066,575; 4,039,561 and 4,350,616. All of the above patents teach the use of cesium in conjunction with the silver coating on the surfaces of the support whether it be applied prior to, simultaneously with or after the application of the silver coating.

One of the problems with catalysts of the above type is that the conditions of use, e.g. high temperature, cause leaching of the cesium component and/or migration thereof.

The present invention is the discovery that the benefits of cesium addition may be obtained without the disadvantages of the known art by adding cesium compounds to the support during its manufacture. In addition the incorporation of the cesium compound into the support provides it with improved crush strength.

SUMMARY OF THE INVENTION

A cesium compound, e.g. cesium hydroxide (CsOH), is added to alumina ($Al_2O_3$) along with other permanent and temporary binders, e.g. inorganic clays and cellulose, respectively, and the mixture fired at high temperature (>1000° C.). Either low or high purity alumina supports may be made with similar advantages in properties with respect to crush strength. A promoter effect is also provided by the cesium when the support is employed as a silver catalyst used for ethylene oxide production.

DETAILED DESCRIPTION OF THE INVENTION

In preparing the improved catalyst support of the present invention one can employ either low purity (~88% $Al_2O_3$) or high purity alumina (99+% $Al_2O_3$) either with or without a silicate compound as a binder together with other binders and porosity controlling agents. The temporary binders employed are those of the prior art such as cellulose, stearates, waxes and the like which are decomposable to water and $CO_2$ at the temperatures employed. These are responsible for producing the porosity of the support material. The permanent binders, inorganic clay-type materials, are partly replaced by cesium compounds, e.g. CsOH. The useful compounds of cesium are fusible at temperatures well below the fusion temperature of alumina itself and include, in addition to cesium hydroxide, the oxides, carbonate, bicarbonate, nitrate sulfate, aluminate and silicate of cesium.

The amount of cesium which is added to the support in the form of one of its compounds, as indicated above, is from about 0.02 to about 0.6 percent by weight based on the finished support. A preferred amount, same basis, is from about 0.03 to about 0.4 percent.

EXAMPLE 1

(Catalyst Preparation)

A low purity alumina support was made using α-alumina and silicate binder and porosity controlling materials according to known methods, but to which sufficient CsOH had been added to provide 0.4% by weight cesium in the finished support. The finished low purity alumina support had a surface area of 0.270 $m^2/g$, a total pore volume of 0.442 cc/g (by Hg intrusion), an average pore diameter of 7.5μ and a crush strength of 26.9 pounds. The 3/16" diameter spheres of low purity alumina (~88% $Al_2O_3$), normally, without the use of the cesium compound, give an average crush strength of about 20 pounds.

EXAMPLE 2

(Leachability of Catalyst)

In an experiment designed to determine leachability, a low purity alumina (~88% $Al_2O_3$) support which had been coated with silver than had a cesium promoter deposited on the silver by washing with a methanol solution of CsOH and then drying. This procedure deposited about 250 ppm Cs on the surface of the silver catalyst. This support silver catalyst was then washed repeatedly with a given volume of water and the amount of cesium removed determined. A catalyst prepared in the same manner, but in which the cesium was present in the support (Example 1) was repeatedly washed with equal volumes of water as above. After 12 washings of this catalyst substantially none of the cesium had been lost, whereas the catalyst having the cesium deposited on the surface of the silver had lost more than half of the cesium after only 2 or 3 washings.
*Method of U.S. Pat. No. 4,350,616.

Catalyst supports of the present invention are especially useful as supports for silver employed as a catalyst in the production of ethylene oxide by the partial oxidation of ethylene in a vapor phase reaction employing oxygen or air as the oxidizing agent.

In accordance with known art silver is applied to the support as a solution of one of its compounds together with various dispersing agents, solubilizing agents, promoters and the like. The silver compound is applied to provide an amount of from about 5 to about 25% by weight or more silver burden upon reduction of the silver compound. Preferred amounts are generally in the range of from about 8 to about 20% by weight based on the total weight of catalyst and support.

EXAMPLE 3

(Use of Catalyst)

Silver catalysts containing cesium were each employed in a process for oxidizing ethylene to ethylene oxide (EO) in the vapor phase. One of the catalysts contained cesium on the surface of the silver while the other contained the cesium as an integral part of the support. The same feed composition was employed in testing each of these catalysts. The yield of EO for each one tested is given below in Table I and is based on a conversion of 25% of the ethylene fed to the reactor:

TABLE I

| Catalyst | % Ag | Cs | Temp. (°C.) | Yield (%) |
|---|---|---|---|---|
| A Prior Art* | 20 | None | 246 | 72 |
| B Prior Art** | 20 | 300 ppm | 252 | 73.5 |
| C Ex. 1* | 16 | 0.4% | 236 | 74.0 |

*Catalyst prepared according to U.S. Pat. No. 4,248,741.
**Catalyst prepared according to U.S. Pat. No. 4,350,616.

Apparently some of the cesium in the support migrates to the surface of the catalyst, providing adequate promotion and does as well or better than those silver catalysts to which it has been added to the surface as in catalyst B in the above Table I. At the same time the cesium is not prone to leaching as with those catalysts to which it is added to the surface.

EXAMPLE 4

In a similar manner high purity alumina compositions containing various amounts of other cesium compounds were prepared and tested for their efficacy as supports for silver in the direct oxidation of ethylene. Silver and promoters were applied to the support in accordance with the prior art referred to in Table I, i.e. U.S. Pat. Nos. 4,248,741 and 4,350,616.

TABLE II

| Example | Cs Source | Cs in* Support (%) | Catalyst Component** Ag (%) | Ba (ppm) | Cs (ppm) | Temp. (°C.) | Conv. (%) | Yield (%) |
| --- | --- | --- | --- | --- | --- | --- | --- | --- |
| 4a | Cs$_2$Al$_2$O$_4$ | 0.035 | 12.5 | — | — | 257 | 29.9 | 79.2 |
| b | " | 0.14 | 12.5 | — | — | 269 | 30.1 | 77.0 |
| c | " | 0.28 | 12.5 | — | — | 265 | 30.3 | 78.4 |
| 5a | " | 0.035 | 12.5 | 1000 | — | 262 | 30.4 | 78.5 |
| b | " | 0.14 | 12.5 | 1000 | — | 260 | 30.2 | 77.5 |
| c | " | 0.28 | 12.5 | 1000 | — | 250 | 30.1 | 78.7 |
| 6a | " | 0.035 | 12.5 | — | 65 | 255 | 30.1 | 79.4 |
| b | " | 0.14 | 12.5 | — | 65 | 243 | 30.0 | 80.3 |
| c | " | 0.28 | 12.5 | — | 65 | 247 | 29.9 | 80.1 |
| 7a | " | 0.035 | 12.5 | 1000 | 65 | 259 | 30.0 | 77.7 |
| b | " | 0.14 | 12.5 | 1000 | 65 | 243 | 30.0 | 79.0 |
| c | " | 0.28 | 12.5 | 1000 | 65 | 243 | 30.2 | 78.2 |
| 8a | Cs$_2$CO$_3$ | 0.04 | 18.0 | — | — | 250 | 30.1 | 77.4 |
| b | " | 0.16 | 18.0 | — | — | 259 | 30.0 | 77.9 |
| c | " | 0.33 | 18.0 | — | — | 245 | 30.4 | 78.6 |
| 9a | " | 0.04 | 18.0 | 1000 | — | 267 | 30.3 | 75.6 |
| b | " | 0.16 | 18.0 | 1000 | — | 263 | 29.5 | 76.4 |
| c | " | 0.33 | 18.0 | 1000 | — | 225 | 29.8 | 74.4 |
| 10a | " | 0.04 | 18.0 | — | 65 | 237 | 29.6 | 78.9 |
| b | " | 0.16 | 18.0 | — | 65 | 245 | 30.5 | 78.9 |
| c | " | 0.33 | 18.0 | — | 70 | 243 | 29.6 | 80.6 |
| 11a | " | 0.04 | 18.0 | 1000 | 65 | 245 | 30.2 | 77.7 |
| b | " | 0.16 | 18.0 | 1000 | 65 | 232 | 30.0 | 78.0 |
| c | " | 0.33 | 18.0 | 1000 | 65 | 239 | 30.2 | 78.4 |
| 12a | Cs$_2$Al$_2$O$_4$ | 0.035 | 18.0 | — | — | 255 | 29.2 | 79.0 |
| b | " | 0.14 | 18.0 | — | — | 262 | 29.7 | 77.2 |
| c | " | 0.28 | 18.0 | — | — | 259 | 30.3 | 78.1 |
| 13a | " | 0.035 | 18.0 | 1000 | — | 243 | 29.8 | 77.0 |
| b | " | 0.14 | 18.0 | 1000 | — | 256 | 30.5 | 76.0 |
| c | " | 0.28 | 18.0 | 1000 | — | 263 | 30.3 | 76.2 |
| 14a | " | 0.035 | 18.0 | — | 65 | 250 | 30.0 | 79.4 |
| b | " | 0.14 | 18.0 | — | 65 | 244 | 30.1 | 80.2 |
| c | " | 0.28 | 18.0 | — | 65 | 250 | 30.5 | 79.2 |
| 15a | " | 0.035 | 18.0 | 1000 | 65 | 240 | 30.3 | 80.0 |
| b | " | 0.14 | 18.0 | 1000 | 65 | 251 | 30.3 | 80.2 |
| c | " | 0.28 | 18.0 | 1000 | 65 | 263 | 29.7 | 79.0 |

*The cesium compound was added to the Al$_2$O$_3$ in preparing the support to provide this amount in the finished support.
**These catalytic components were added to the surface of the support.

EXAMPLE 16

For comparison a high purity alumina support, with no cesium added during its preparation, was used to make a silver catalyst in the manner of U.S. Pat. No. 4,248,741. The finished catalyst contained 18% Ag and 1000 ppm Ba by weight. The same feed composition was used as for all the examples in Table II above. A temperature of 260° C. gave a 30.0% conversion of ethylene and the yield of EO was 76.0%.

The physical properties of the above support materials were determined. Results are shown in Table III below:

TABLE III

| Support of Ex. No. | Source of Cs | Cs in Support (%) | Crush Strength |
| --- | --- | --- | --- |
| 4a | Cs$_2$Al$_2$O$_4$ | 0.035 | 37.6 |
| b | " | 0.14 | 35.2 |
| c | " | 0.28 | 47.9 |
| 8a | Cs$_2$CO$_3$ | 0.04 | 64.5 |
| b | " | 0.16 | 58.2 |
| c | " | 0.33 | 43.9 |

It should be noted that, although the support materials containing the cesium compounds in the range of about 0.03 to about 0.4% Cs in above Table III show an improvement in crush strength over one not containing the cesium compound, the use of a particular compound differs in the magnitude of the effect with respect to the amount of compound added. Thus, while in the case of the aluminate the effect on crush strength varies directly with the amount added, the carbonate gives an effect varying indirectly with the amount added. The improvement, however, in crush strength is noted over the entire range of additions of from about 0.03 to about 0.6% by weight cesium in the finished alumina support.

Even though the cesium incorporated into the support provides some promoter effect to the silver catalyst when used in the process of oxidizing ethylene to ethylene oxide, additional cesium placed on the surface of the catalyst sometimes is beneficial. If the amount of cesium in the support is sufficient to provide an optimum amount with respect to promotion of this oxidation reaction, additional cesium on the surface will be of no benefit and may even be deleterious.

We claim:

1. In the process of making an alumina support material by heating at an elevated temperature of >1000° C. a mixture of alumina, porosity control agents and binders, the improvement which comprises adding a cesium compound to said mixture to provide in the finished support an amount of cesium of from about 0.03 to about 0.6 percent by weight of the total support material, said cesium being in substantially unleachable form as the result of having been incorporated into said support by the fusion of said alumina and cesium compound at said elevated temperature.

2. The process of claim 1 wherein the cesium compound is an oxide, hydroxide, carbonate, bicarbonate, nitrate, sulfate, aluminate or silicate of cesium.

3. The process of claim 2 wherein the alumina support contains 99% by weight or more Al$_2$O$_3$.

4. The process of claim 2 wherein the alumina support contains silica and other impurities, but at least about 88% by weight $Al_2O_3$.

5. The process of claim 4 wherein the compound of cesium is CsOH.

6. The process of claim 3 wherein the compound of cesium is $Cs_2Al_2O_4$.

7. The process of claim 3 wherein the compound of cesium is $Cs_2CO_3$.

8. An improved catalyst support comprising at least about 88% $Al_2O_3$ and from about 0.02 to about 0.6 percent by weight cesium in an unleachable form.

9. The catalyst support material of claim 8 wherein cesium is present in an amount of from about 0.03 to 0.4 percent.

10. The catalyst support of claim 8 which contains at least about 99 percent $Al_2O_3$ by weight.

11. The catalyst support of claim 10 wherein the cesium is present in an amount of from about 0.03 to about 0.4 percent by weight.

12. A catalyst formed from the support of claim 8 containing a burden of silver of from about 5 to about 25% by weight based on total weight of silver and support.

13. The catalyst of claim 12 containing from about 8 to about 20% by weight silver.

* * * * *

UNITED STATES PATENT AND TRADEMARK OFFICE
CERTIFICATE OF CORRECTION

PATENT NO. : 4,575,494

DATED : March 11, 1986

INVENTOR(S) : Harold W. Young, Jr.; Oliver C. Ainsworth, Jr.;
William E. Fry and Lawrence E. Neil It is certified that error appears in the above-identified patent and that said Letters Patent is hereby corrected as shown below:

Col. 2, line 57, change "Nos. 4,010,155;" to --Nos. 4,010,115;--.

Col. 3, line 67, change "than" to --then--.

Col. 3, line 67, after the word "promoter" add an --*-- (asterisk).

Col. 4, line 3, change "support" to --supported--.

Signed and Sealed this

Twenty-first Day of October, 1986

[SEAL]

Attest:

DONALD J. QUIGG

Attesting Officer     Commissioner of Patents and Trademarks